(12) United States Patent
Alem et al.

(10) Patent No.: US 9,791,536 B1
(45) Date of Patent: Oct. 17, 2017

(54) MUTUALLY CALIBRATED MAGNETIC IMAGING ARRAY

(71) Applicant: QuSpin, Inc., Louiville, CO (US)

(72) Inventors: Orang Alem, Lafayette, CO (US);
Vishal Shah, Westminster, CO (US);
Svenja Knappe, Boulder, CO (US)

(73) Assignee: QuSpin, Inc., Louisville, CO (US)

( * ) Notice: Subject to any disclaimer, the term of this patent is extended or adjusted under 35 U.S.C. 154(b) by 0 days.

(21) Appl. No.: 15/581,074

(22) Filed: Apr. 28, 2017

(51) Int. Cl.
*G01V 3/00* (2006.01)
*G01R 35/00* (2006.01)
*G01R 33/032* (2006.01)
*A61B 5/04* (2006.01)

(52) U.S. Cl.
CPC ........ *G01R 35/005* (2013.01); *A61B 5/04008* (2013.01); *G01R 33/032* (2013.01); *A61B 2560/0223* (2013.01); *A61B 2562/0223* (2013.01)

(58) Field of Classification Search
CPC .................................................. A61B 5/04008
USPC .................................................. 324/304, 301
See application file for complete search history.

(56) References Cited

U.S. PATENT DOCUMENTS

| | | | |
|---|---|---|---|
| 4,951,674 | A | 8/1990 | Zanakis et al. |
| 6,966,211 | B2 | 11/2005 | Wu |
| 7,030,378 | B2 | 4/2006 | Allen et al. |
| 7,197,352 | B2 | 3/2007 | Gott et al. |
| 7,783,457 | B2 | 8/2010 | Cunningham |
| 8,284,026 | B2 | 10/2012 | Ivanov et al. |
| 8,379,485 | B2 | 2/2013 | Cevher et al. |
| 8,446,253 | B2 | 5/2013 | Ramchandran et al. |
| 8,447,330 | B2 | 5/2013 | Chakravartv et al. |
| 8,717,009 | B2 | 5/2014 | Tu |
| 8,786,719 | B2 | 7/2014 | Chao et al. |

(Continued)

FOREIGN PATENT DOCUMENTS

EP   1591062 B1   11/2005

OTHER PUBLICATIONS

Adachi et al. IEEE Trans. on Magnetics, vol. 50, No. 11, Nov. 2014, Calibration for a Multichannel Magnetic Sensor Array of a Magnetospinography System.

(Continued)

*Primary Examiner* — Louis Arana
(74) *Attorney, Agent, or Firm* — Patricia Brzostowicz; Superior Patent Group

(57) ABSTRACT

A mutually calibrated magnetic imaging array system is described. The system includes a non-target magnetic source rigidly attached to a magnetometer, and an attached control unit to measure and adjust several parameters of a magnetic imaging array. A non-target magnetic field source is used to generate a well-defined and distinguishable spatial magnetic field distribution. The source is rigidly attached directly to a magnetometer, while the relative positions of the magnetometers are unknown. The magnetic imaging array is used to measure the strength of the non-target source magnetic fields and the information is used to calibrate several parameters of the array, such as, but not limited to, effective magnetometer positions and orientations with respect to each other and cross-talk between the magnetometers. The system, and method described herein eliminates the need for a separate calibration phantom.

20 Claims, 5 Drawing Sheets

(56) References Cited

U.S. PATENT DOCUMENTS

| | | | |
|---|---|---|---|
| 9,167,979 B2* | 10/2015 | Skidmore | A61B 5/04009 |
| 9,229,084 B2 | 1/2016 | Tu | |
| 9,370,309 B2* | 6/2016 | Ko | A61B 5/04008 |
| 2003/0152248 A1 | 8/2003 | Spark et al. | |
| 2010/0137707 A1 | 6/2010 | Hunter et al. | |
| 2016/0169797 A1 | 6/2016 | Chau et al. | |
| 2016/0291123 A1 | 10/2016 | Van Puijenbroek | |

OTHER PUBLICATIONS

Alem, Orang vol. 25, No. 7 | Apr. 3, 2017 | Optics Express 7849 Magnetic field imaging with microfabricated optically-pumped magnetometers.

Boto, et al. On the Potential of a New Generation of Magnetometers for MEG: A Beam former Simulation Study, Published: Aug. 26, 2016, Copyright: © 2016 Boto et al. This is an open access article distributed under the terms of the creative Commons Attribution License.

A. C. Bruno and P. Costa Ribeiro Spatial Fourier calibration method for multichannel SQUID magnetometers, Citation: 62, 1005 (1991); doi: 10.1063/1.1142049, Published by the American Institute of Physics.

Chella et al. Phys. Med. Biol. 57 (2012) 4855-4870 Calibration of a multichannel MEG system based on the Signal Space Separation method.

Kim et al. Multi-channel atomic magnetometer for magnetoencephalography: A configuration study NeuroImage 89 (2014) 143-151.

Kraus et al. Source Localization Precision of the Superconducting Imaging-Surface MEG System http://lib-www.lanl.gov/cgi-bin/getfile?00796808.pdf.

Pasquarelli et al. Calibration of a Vector-MEG Helmet System Neurology and Clinical Neurophysiology 2004:94 (Nov. 30, 2004).

Vivaldi Calibrating the new MEG system in Naples poster present at http://mida.dima.unige.it 2014.

* cited by examiner

MUTUALLY CALIBRATED MAGNETIC IMAGING ARRAY

The following application is an application for patent under 35 USC 111 (a). This invention was made with government support under HD074495 awarded by the National Institutes of Health. The government has certain rights in the invention

FIELD OF INVENTION

This disclosure relates to the field of magnetic imaging arrays, specifically a device used to create an array, and method thereof.

BACKGROUND

Optically pumped magnetometers (OPMs), also called atomic magnetometers, optical magnetometers, or optical atomic magnetometers, are used in a number of scientific and advanced technology applications including medical imaging. In their simplest form, they contain a light source, a container to hold atoms, and a detector. The light source may be a laser or other optical device used to produce light of a certain wavelength. The container may be a vapor cell or other device used to house atoms. The detector would necessarily be specific to the light output.

Single OPMs or small arrays of OPMs have been used routinely to create magnetic field images or gradient magnetic field images and to localize magnetic sources. In many cases, the sensors or sensor arrays are mounted onto moving platforms and moved in regular patterns over the area of interest. Alternatively, larger arrays allow the sensors to be stationary. In order to localize magnetic sources, the positions of the sensors have to be known. For large area images, the sensor location can be determined with global navigation satellite systems (GNSS), such as but not limited to the global positioning system (GPS). For smaller areas of interest, sensor positions have been determined geometrically or optically. For some OPMs, an additional complication comes from the fact that the position at which the magnetic field is measured is determined by the position of the laser beam, not a physical component of the sensor.

There are several other factors that determine the quality of the image and the source localization apart from the locations of the sensors in the array, such as but not limited to, sensor orientation, sensor gain as a function of frequency, sensor bandwidth, sensor cross-talk, and sensor linearity. All these sensor array parameters are usually calibrated at least once before the measurement.

SUMMARY OF THE INVENTION

One application of imaging magnetic sources with a large number of magnetometers is magnetoencephalography (MEG), where hundreds of magnetometers are used to measure magnetic fields produced by brain tissue. Magnetometers traditionally used in MEG were superconducting quantum interference devices. These magnetometers are rigidly mounted in fixed shells, called Dewars. Several standard methods have been developed to calibrate the magnetometer positions, orientation, and gains of the imaging array. Most of them use a fixed and calibrated set of dipolar sources built into rigid fixed enclosures, often called phantoms. The relative positions and orientations of the sources are precisely known prior to data collection. The magnetic field distributions are measured with the magnetometer array and the values are compared to theoretical models. This allowed estimation of the magnetometer positions and orientation with respect to each other and the source array. Others used a method to compensate for external interference and sensor artifacts to determine the magnetometer positions (A. Bruno and P. Costa Ribeiro, *Rev. Sci. Instrum.*, Vol. 62, 1005, 1991; R. Kraus Jr. et al., *Biomedizinische Technik* 46, 38, 2001; A. Pasquarelli et al., *Neurology and Clinical Neurophysiology*, 94, 1, 2004; Y. Adachi et al., *IEEE Trans. Mag.* 50, 5001304, 2014; V. Vivaldi, *Biomag* 2014, August 24-28, Halifax, Canada).

These large stationary magnetic imaging arrays do not change their configuration and drifts are slow, so that calibration does not have to be performed frequently and the phantom approach is a viable one. Optically-pumped magnetometers are small and not cooled. They can be arranged into flexible arrays, which results in the need to determine all sensor positions and orientations every time the array configuration is changed. In addition, the orientation of the sensing axes of each magnetometer in the array is affected by cross-talk from neighboring sensors. These parameters require more frequent calibration for every measurement in order to create high-resolution images, making a phantom-type approach tedious.

In prior art, Kim et al. (K. Kim et al, *NeuroImage* 89, 143 (2014)) have calibrated the position and orientation of an OPM-based sensor array by applying calibrated linear magnetic field gradients to the array with a large set of coils around the whole sensor array. The magnetometers were then utilized to determine the magnetic field at the location of the atoms. This allowed deduction of the exact "effective" sensor positions and orientations at the time of calibration.

The above methods calibrate the array with a separate external device that allows the exact knowledge of the field it produces since the locations and orientation of all sources with respect to each other and the field pattern they create are known precisely. This field is then used to determine the orientations, positions, and gains of the magnetometers. In several previous MEG applications, OPM positions and orientations have been determined geometrically before or after the measurement. In Boto et al, (E. Boto et al., *PLOS ONE* 11, e0157655, 2016) a snug-fitting printed headcast was used to tightly constrain the outer dimensions of the sensors and the effective sensor position was calculated from that. In O. Alem et al., (O. Alem et al., *Optics Express*, 25, 7849 (2017)) a printed helmet allowed for sensor movement in the radial direction only and the radial position was recorded after every measurement. The sensor positions were then inferred from the geometric geometry.

The present invention is a system wherein at least one non-target magnetic field source is integrally connected to a magnetic sensor, or magnetometers, i.e., are one piece. The orientation and location of the source with respect to the magnetometer is known, but the location of the source with respect to the other non-target sources in the array is not. This is a major difference to calibration with a phantom. Further, the system comprises a computation unit to calculate parameters used to calibrate the imaging array. This imaging array device reduces the bulk of imaging array systems by integrating the calibration phantom directly on the magnetometers and using the sensors themselves to triangulate between each other. It eliminates the need for a separate calibration system and enables the imaging array to be more transportable and less cumbersome, especially for applications such as magnetoencephalography. It furthermore makes operation of the array easier and faster.

The system, and method described herein is broadly applicable to imaging systems with one or more sensors, such as magnetometers, positioned in different locations. The system and method described herein may also be particularly useful in situations in which the exact magnetometer locations or other parameters of the imaging array vary from one measurement to the next. These parameters are usually the positions and orientations of the magnetometers, but could also include their cross-talk.

Briefly describing the invention, a magnetic imaging array consists of at least two magnetometers. At least one of the magnetometers has a non-target source rigidly attached to it so that the magnetic field pattern of the non-target source with respect to the attached magnetometer is known precisely. The second magnetometer then senses this magnetic field pattern and the information is used to calibrate the orientation and location of one magnetometer with respect to the other.

Specifically, the invention comprises, a magnetic imaging system, the system comprising: at least one non-target magnetic source capable of creating a known magnetic field pattern; at least one magnetometer, wherein the magnetometer is rigidly attached to the at least one non-target magnetic source; at least one additional magnetometer, wherein the additional magnetometer is used to detect the magnetic field generated by the at least one non-target magnetic source, and a computational unit that uses the magnetic field measurement from the non-target magnetic source to generate at least one calibration parameter of the magnetic imaging array. Further the invention comprises, a method of calibrating a magnetic imaging array, the method comprising the steps of: using at least one non-target magnetic source attached to at least one magnetometer to create a known magnetic field pattern; using at least one additional magnetometer to measure the magnetic field created by the non-target source; and using the magnetic field measurement from the at least one non-target magnetic source to produce a calibration parameter of the imaging array.

Before explaining the disclosed embodiments of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE INVENTION

Figure 1:
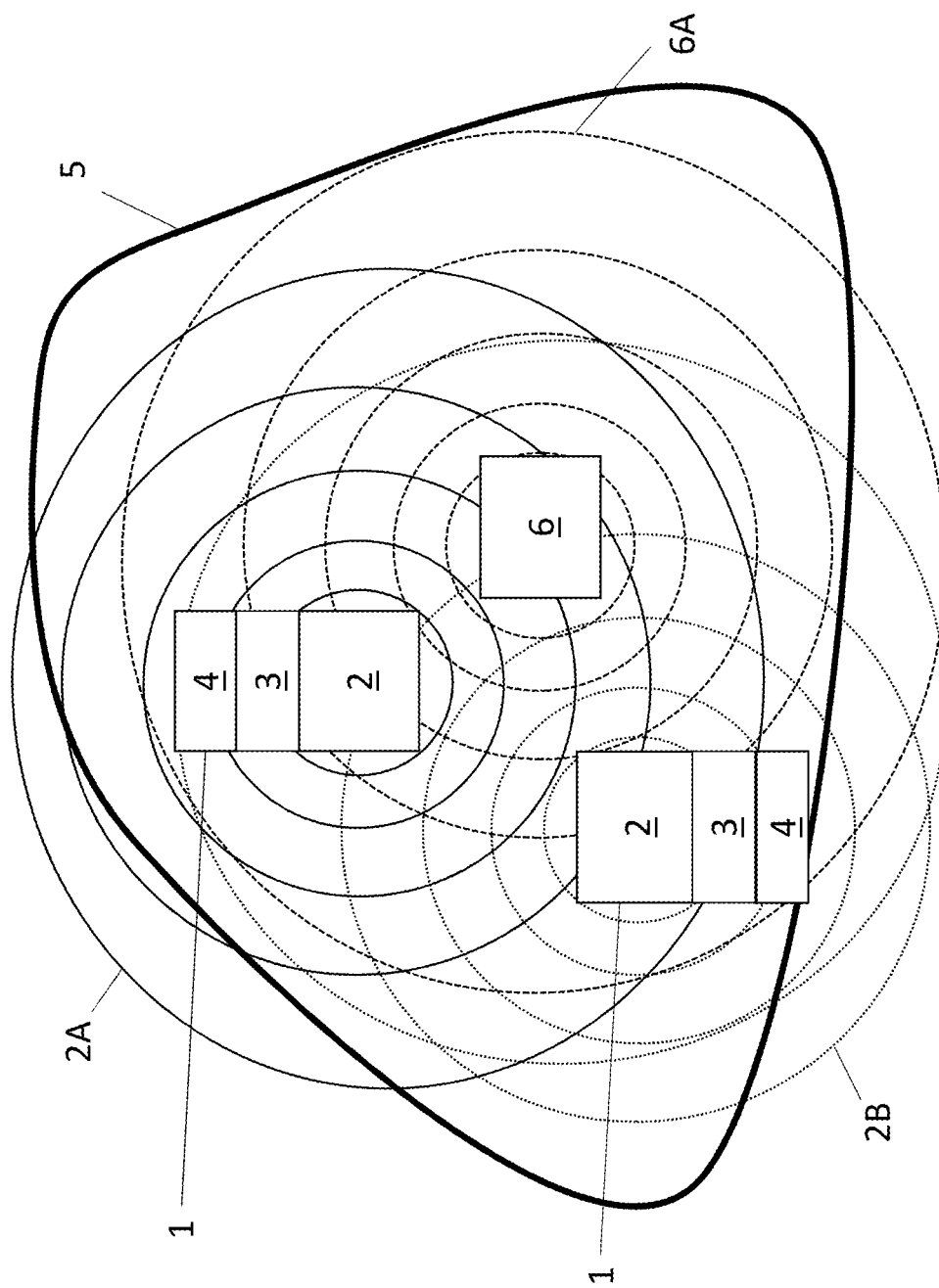
FIG. 1 is a schematic diagram illustrating the invention.

FIG. 1 is a schematic diagram illustrating the invention. One or more magnetic array devices 1 make up an imaging array. These magnetic array devices 1 include at least one non-target magnetic source 2, at least one magnetometer 3, and a computational unit 4 capable of generating calibration parameters of the array. In this device 1, the at least one non-target magnetic source 2 is rigidly connected to the magnetometer 3 such that the positions and orientation of the source with respect to the magnetometer 3 are known. In use, the non-target magnetic source(s) 2 create magnetic field patterns 2A and 2B, such that the magnetic field from each source is known over an area of interest 5. The magnetometers 3 measure the magnetic field emitted by the magnetic sources 2. These magnetic sources may be dipole sources such as field coils. The magnetic fields patterns, 2A and 2B, are non-target magnetic fields created in such a way that they can be distinguished from the target magnetic field(s) 6A created by a target magnetic source(s) 6. A non-target magnetic field 2 or source is defined as a source, or magnetic field generated by a source, that is part of the input to a system, in other words in addition to any other background or target source of interest.

In order to distinguish between the non-target and target sources and not limit the measurements, the sources may generate fields within a narrow frequency band, where each non-target source could have its own frequency band outside the target measurement band of interest (frequency multiplexing). Alternatively, all sources could use the same frequency band and the sources are emitting successively, where only one non-target source is emitting at any given time.

The non-target magnetic field information sensed by each of the magnetometers 3 can be used to calibrate parameters of the imaging array with the computation unit 4. The computation unit 4 may be connected via wires or have the ability to wirelessly communicate with the magnetometers 3. The computation unit 4 may be programmed to record calibration data and/or calculate change in control parameters of the array. The control parameters are nominally the magnetometer positions and orientations, but can also include but are not limited to cross-talk between the magnetometers.

Figure 2:
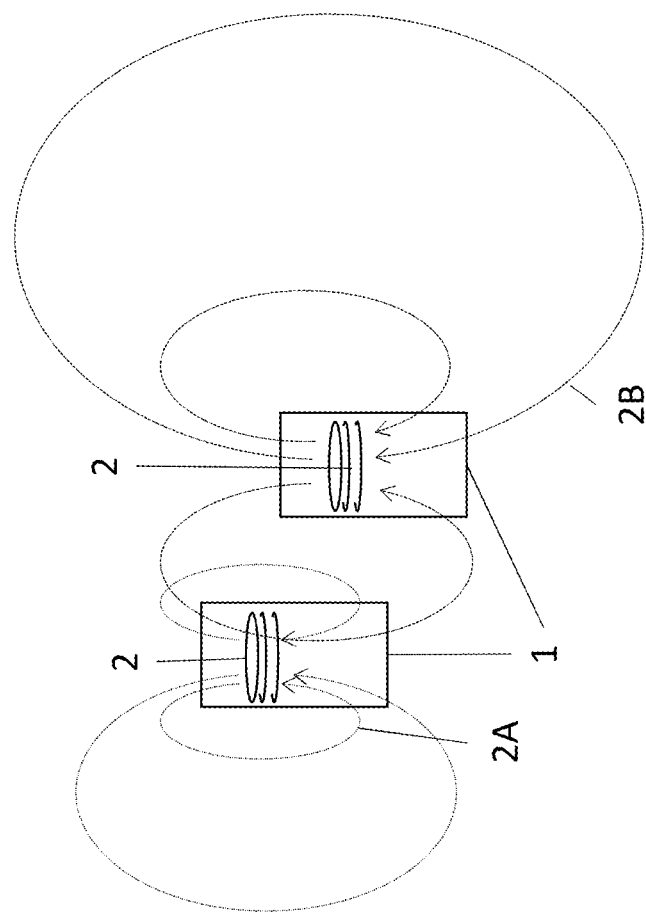
FIG. 2 is a schematic diagram illustrating several components of one embodiment of the invention.

FIG. 2 is a schematic diagram illustrating a first embodiment of the invention. Two array devices 1, are fitted with non-target magnetic sources 2 generating a magnetic field with a well-defined spatial pattern 2A, 2B. In this case, the non-target magnetic source are magnetic coils. On the array device, as described above, a magnetometer (not shown) is rigidly attached to the non-target source 2, such that the position and orientation of the source with respect to the magnetometer is known. Each magnetometer measures the value of the magnetic field of the non-target sources 2 at its location. The strength of the field measured with the magnetometer contains information about parameters of the other magnetometer, such as the position and orientation of the two magnetometers with respect to each other. A computation unit integral to the device (not shown) generates information that can be used to calibrate one or more parameters of the array. Such parameters could be, but are not limited to, the magnetometer position and orientation with respect to the non-target source 2, and therefore the other magnetometer and it can also include the cross-talk between the magnetometers.

Figure 3:
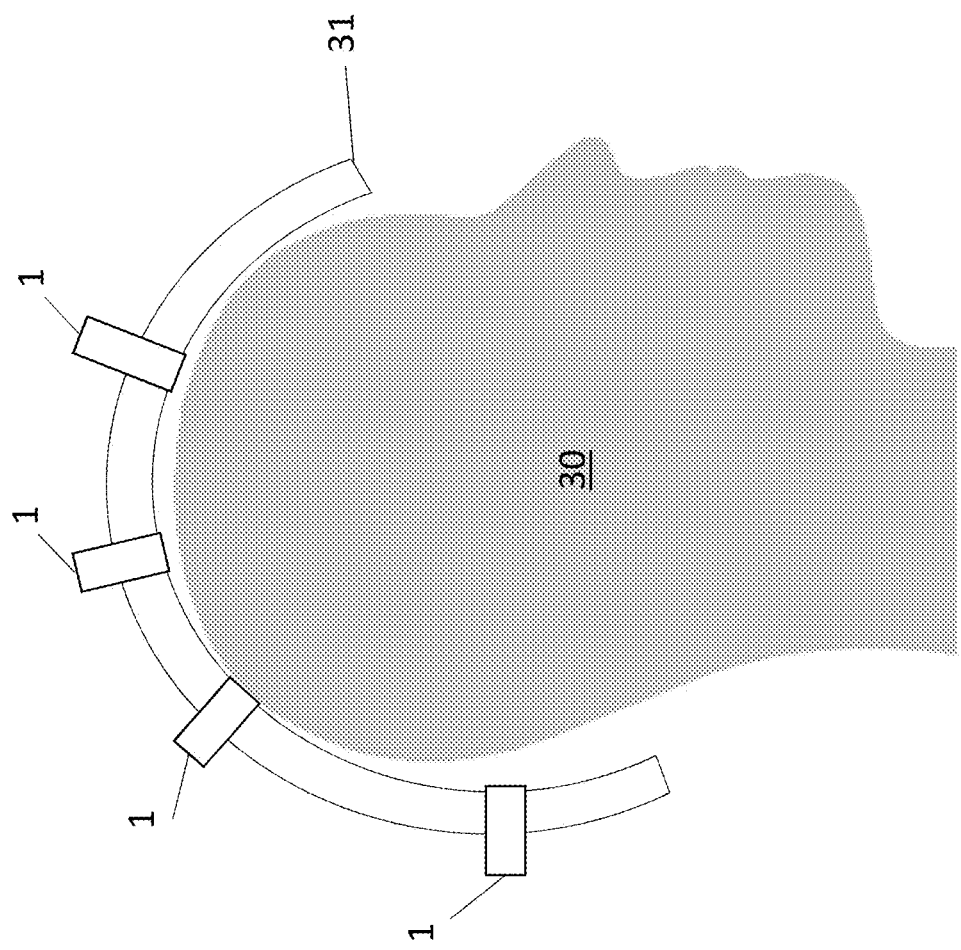
FIG. 3 is a schematic diagram illustrating several components of a second embodiment of the invention.

FIG. 3. is an illustration of a second embodiment of the invention. For magnetoencephalography, helmets or caps 31 with imaging arrays containing a number of array devices 1, described above, can be utilized to measure magnetic fields produced by the brain tissues of a human subject 30. The array devices 1 including non-target magnetic field sources, rigidly attached to magnetometers and computation unit, are placed in the cap 31. The magnetometers are intended to measure the magnetic field emitted by brain tissue, or other matter in the subject's 30 brain. The magnetometers are also used to record the field produced by the one or more non-target magnetic field sources emanating from each of the array devices 1. This source may be a dipole source such as field coils. The magnetometer may be an optically-pumped magnetometer (OPM) or any other small-sized magnetometer. This magnetometer data is used by the computation unit (not shown) to calibrate one or more parameters such as but are not limited to, the magnetometer position and orientation with respect to the non-target source, and therefore each other, and the magnetometer cross-talk. In practice, not every magnetometer in the cap 31 need be fitted with non-target sources.

EXAMPLES

Example 1

Figure 4:
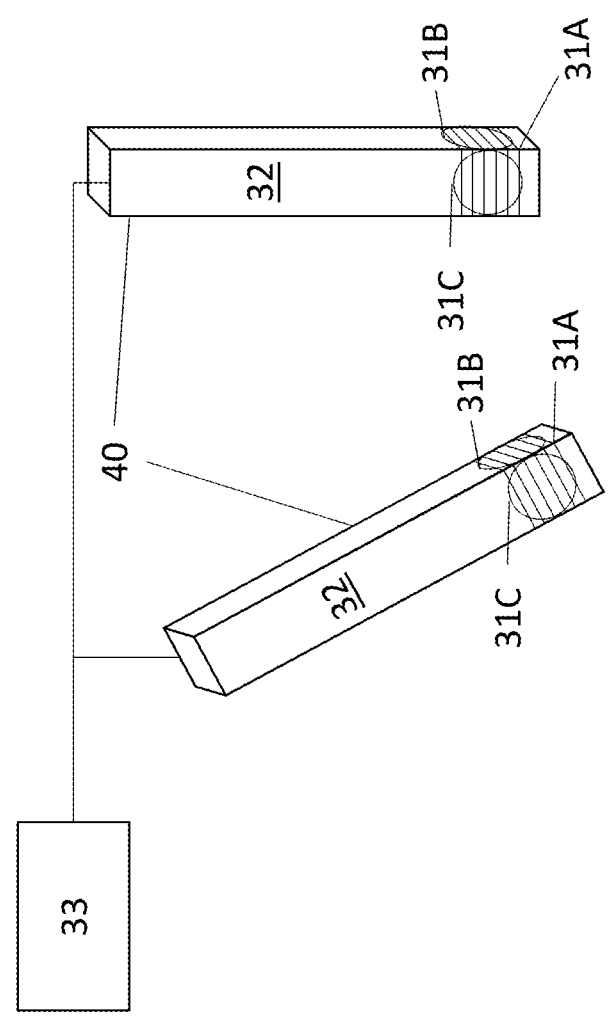
FIG. 4 is a schematic diagram illustrating an optically-pumped magnetometer imaging array with a set of dipolar sources as an embodiment of the system and method for calibrating the positions and orientations of the magnetometers of the imaging array with respect to one another directly integrated into the magnetometers.

As an example, a simple magnetic imaging array made up of magnetic array devices 40, as described above, has been constructed out of two optically-pumped magnetometers (OPMs) 32, magnetic coils 31A, 31B, and 31C, and a computation unit 33, as shown in FIG. 4. Each OPM 32 measured the field in two nearly orthogonal directions. A schematic diagram of the imaging array is shown in FIG. 4. Three coils 31A, 31B, and 31C, were wrapped around each of the OPM magnetometers 32 in nearly orthogonal directions serving as three non-target sources. The relative positions and orientations of each coil with respect to the OPM magnetometer 32 it is attached to are measured carefully. In this way, the magnetic field of each of the dipolar sources was known relative to the magnetometer itself. Oscillating non-target magnetic fields were applied to the six dipoles at frequencies of 80 Hz, 81 Hz, 83 Hz, 84 Hz, 86 Hz, and 87 Hz, respectively. The fields were recorded continuously in each of the four channels of the two OPM magnetometers 32 by the attached computation unit 33. For purposes of the prototype in this example, the devices 40 were connected to a remote controller via wires, but miniaturized attached computation units are also viable options. The data stream was recoded with a data acquisition system. In order to calibrate the imaging array, the computation unit 33 generated a Fourier spectrum from the time series. One may envision, wired or wireless communication between a computation unit 33 attached to a device 40 and a data acquisition and output system.

Figure 5:
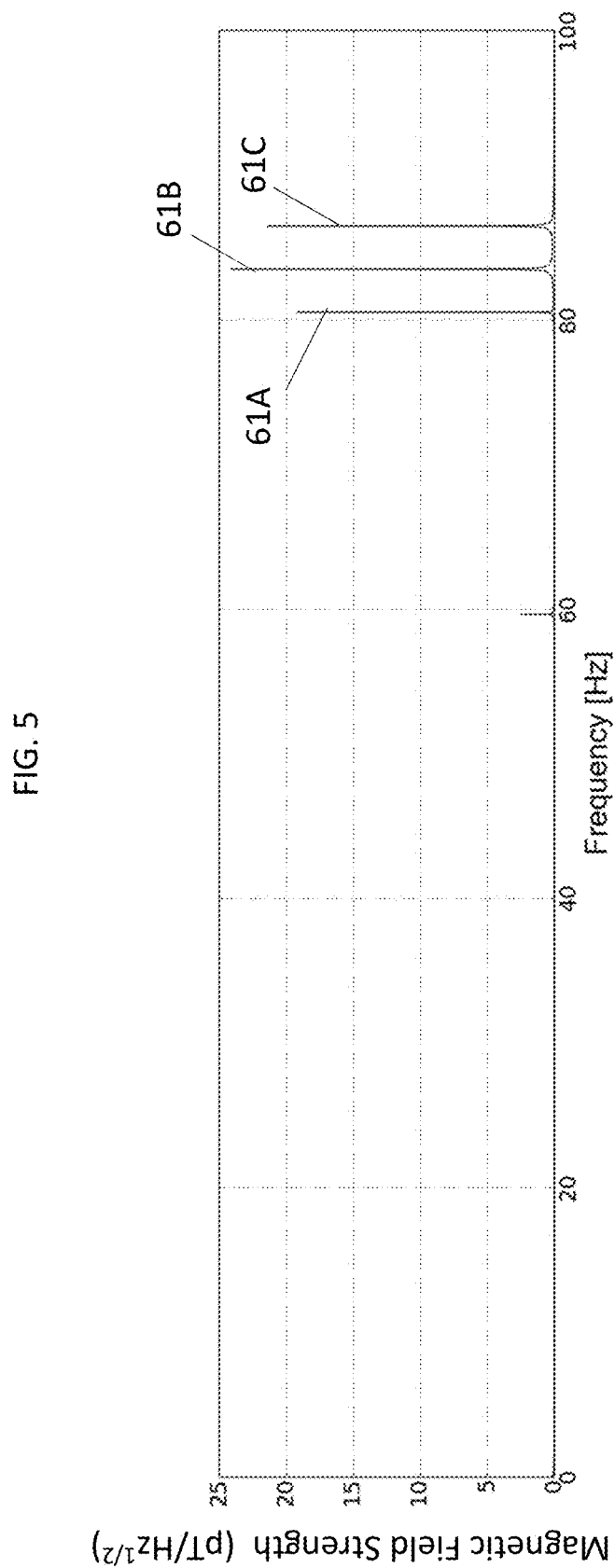
FIG. 5 is the magnetic fields strength measured by one of the magnetometers as a function of frequency with responses from two non-target magnetic sources driven at three different frequencies.

A measured spectrum of the magnetic field strength of one of the sensors is shown in FIG. 5 with just one non-target sources active at 81 Hz, 84 Hz, and 87 Hz, 61A, 61B, and 61C. The peaks at the modulation frequencies can be seen clearly. A computation unit 33 furthermore determined the amplitudes of the peaks. Finally, the computation unit 33 used these amplitudes to fit the effective positions and orientations of the OPM magnetometers 32 with respect to each other. Once the parameters of the imaging array were known, the array was used to image unknown fields in the same configuration. Standard source localization algorithms were used. The input parameters were given by the calibrated parameter of the imaging array.

Although the present invention has been described with reference to the disclosed embodiments, numerous modifications and variations can be made and still the result will come within the scope of the invention. No limitation with respect to the specific embodiments disclosed herein is intended or should be inferred. Each apparatus embodiment described herein has numerous equivalents.

What is claimed is:

1. A magnetic imaging system, the system comprising:
   a. at least one non-target magnetic source capable of creating a known magnetic field pattern;
   b. at least one magnetometer, wherein the magnetometer is rigidly attached to the at least one non-target magnetic source;
   c. at least one additional magnetometer, wherein the additional magnetometer is capable of detecting the known magnetic field pattern and creating a magnetic field measurement; and
   d. a computational unit that uses the magnetic field measurement to generate at least one calibration parameter of the magnetic imaging system.

2. The system of claim 1, wherein the magnetometers are optically-pumped magnetometers.

3. The system of claim 1, wherein the at least one non-target magnetic source is a dipolar source.

4. The system of claim 1, wherein the at least one non-target magnetic source is a field coil of the at least one magnetometer.

5. The system of claim 1, wherein the calibration parameter of the magnetic imaging system is related to the relative position of the magnetometers.

6. The system of claim 1, wherein the calibration parameter of the magnetic imaging system is the relative orientation of the magnetometers.

7. The system of claim 1, wherein the calibration parameter of the magnetic imaging system is the cross-talk between the magnetometers.

8. The system of claim 1, wherein the computational unit is attached to the at least one magnetic source and the at least one magnetometer.

9. A magnetic imaging system, the system comprising:
   a. a flexible housing;
   b. at least one device, the device comprising a magnetic source and a magnetometer rigidly attached to one another;
   c. at least one additional magnetometer capable of taking a magnetic field measurement of the magnetic source; and
   d. a computational unit that uses the magnetic field measurement to generate at least one calibration parameter of the magnetic imaging system; and
   wherein, the device and the at least one additional magnetometer are fitted to the flexible housing in a secure manner.

10. The system of claim 9, wherein the magnetometers are optically-pumped magnetometers.

11. The system of claim 9, wherein the at least one non-target magnetic source is a dipolar source.

12. The system of claim 9, wherein the at least one non-target magnetic source is a field coil of the device.

13. The system of claim 9, wherein the computational unit is attached to the device.

14. A method of calibrating a magnetic imaging array, the method comprising the steps of:
   a. rigidly attaching at least one non-target magnetic source to as least one magnetometer;
   b. using the least one non-target magnetic source to create a known magnetic field pattern;
   c. using at least one additional magnetometer to measure the magnetic field of the non-target source to create a magnetic field measurement; and d. using the magnetic field measurement to produce a calibration parameter of the imaging array.

15. The method of claim 10, wherein step c uses an optically-pumped magnetometer.

16. The method of claim 10, wherein step b is achieved with a dipole source.

17. The method of claim 10, wherein step b is achieved with a field coil.

18. The method of claim 10, wherein step d produces the relative position of the magnetometers as the calibration parameter.

19. The method of claim 10, wherein step d produces the relative orientation of the magnetometers as the calibration parameter.

20. The method of claim 10, wherein step d produces the cross-talk between the magnetometers as the calibration parameter.

* * * * *